United States Patent
Nagasaka et al.

(10) Patent No.: US 12,054,703 B2
(45) Date of Patent: Aug. 6, 2024

(54) **AGRICULTURAL OR HORTICULTURAL COMPOSITION CONTAINING CULTURE BROTH OF *Bacillus* BACTERIUM**

(71) Applicant: AJINOMOTO CO., INC., Tokyo (JP)

(72) Inventors: Yuta Nagasaka, Kanagawa (JP); Daisuke Kitazawa, Kanagawa (JP); Kenichi Kaida, Kanagawa (JP); Atsushi Hayakawa, Kanagawa (JP); Daisuke Igarashi, Kanagawa (JP); Natalia Sergeevna Eremina, Moscow (RU); Natalia Viktorovna Stoynova, Moscow (RU); Kseniia Viktorovna Emelina, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 873 days.

(21) Appl. No.: 17/036,971

(22) Filed: Sep. 29, 2020

(65) Prior Publication Data

US 2021/0015107 A1  Jan. 21, 2021

Related U.S. Application Data

(63) Continuation of application No. PCT/JP2019/014974, filed on Apr. 4, 2019.

(30) Foreign Application Priority Data

Apr. 6, 2018 (RU) ................................ 2018112485

(51) Int. Cl.
    C12N 1/20      (2006.01)
    A01N 63/22     (2020.01)
    C12N 9/88      (2006.01)

(52) U.S. Cl.
    CPC .............. *C12N 1/20* (2013.01); *A01N 63/22* (2020.01); *C12N 9/88* (2013.01); *C12Y 402/01051* (2013.01)

(58) Field of Classification Search
    None
    See application file for complete search history.

(56) References Cited

U.S. PATENT DOCUMENTS 4,681,852 A   7/1987   Tribe

FOREIGN PATENT DOCUMENTS

CN   103204732 A  *  7/2013
WO   WO2008/106463 A1   9/2008

OTHER PUBLICATIONS

Solanki et al., Current Microbiology (2012), vol. 65, No. 3, pp. 330-336, 20 refs. (Year: 2012).*
Yunlong et al., Frontiers in Microbiology (2015), vol. 6, No. August, pp. 883 (Year: 2015).*
LuYao et al., Chinese Journal of Biological Control (2017), vol. 33, No. 2/3, pp. 234-240, 29 refs (Year: 2017).*
Buensanteai et al., Proceedings of the 45th Kasetsart University Annual Conference, Bangkok, ThaiThailand, Jan. 30-Feb. 2, 2007. Subject: Plants (2007), pp. 364-371, 10 refs. (Year: 2007).*
Chowdhury, S. P., et al., "Biocontrol mechanism by root-associated *Bacillus amyloliquefaciens* FZB42—a review," Frontiers in Microbiol. 2015, vol. 6, 780 (11 pp).
Idris, E. E., et al., "Tryptophan-Dependent Production of Indole-3-Acetic Acid (IAA) Affects Level of Plant Growth Promotion by *Bacillus amyloliquefaciens* FZB42," MPMI 2007;20(6):619-626.
Talboys, P. J., et al., "Auxin secretion by *Bacillus amyloliquefaciens* FZB42 both stimulates root exudation and limits phosphorous uptake in Triticum aestivium," BMC Plant Biol. 2014, vol. 14, 51 (9 pp).
Shao, J., et al., "Analysis and cloning of the synthetic pathway of the phytohormone indole-3-acetic acid in the plant beneficial *Bacillus amyloliquefaciens* SQR9*," Microb. Cell Fact. 2015, vol. 14, 130 (13 pp).
Nelms, J., et al., "Novel Mutations in the pheA Gene of *Escherichia coli* K-12 Which Result in Highly Feedback Inhibition-Resistant Variants of Chorismate Mutase/Prephenate Dehydratase," Appl. Environmen. Microbiol. 1992;58(8):2592-2598.
International Search Report and Written Opinion for PCT Patent App. No. PCT/JP2019/014974 (Jul. 11, 2019).

* cited by examiner

*Primary Examiner* — Alton N Pryor
(74) *Attorney, Agent, or Firm* — Cermak & McGowan LLP; Shelly Guest Cermak

(57) ABSTRACT

An agricultural or horticultural composition is provided. A composition containing a culture broth of a *Bacillus* bacterium having prephenate dehydratase (PD) resistant to feedback inhibition by phenylalanine.

11 Claims, 1 Drawing Sheet
Specification includes a Sequence Listing.

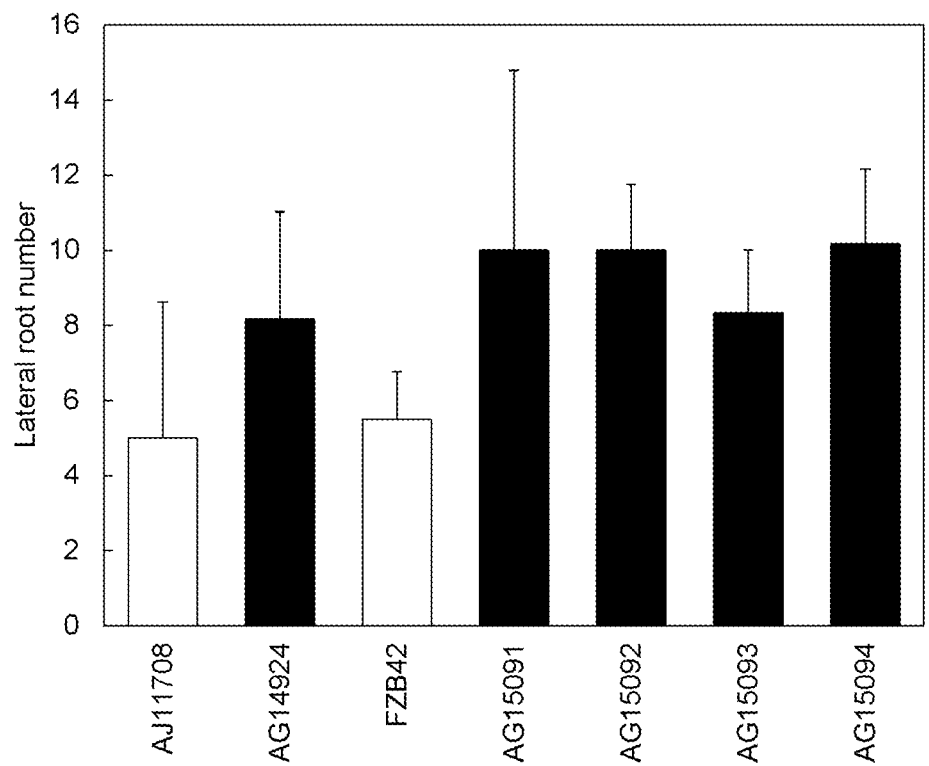

AGRICULTURAL OR HORTICULTURAL COMPOSITION CONTAINING CULTURE BROTH OF *Bacillus* BACTERIUM This application is a Continuation of, and claims priority under 35 U.S.C. § 120 to, International Application No. PCT/JP2019/014974, filed Apr. 4, 2019, and claims priority therethrough under 35 U.S.C. § 119 to Russian Patent Application No. 2018112485, filed Apr. 6, 2018, the entireties of which are incorporated by reference herein. Also, the Sequence Listing filed electronically herewith is hereby incorporated by reference (File name: 2020-09-29T_US-617_Seq_List; File size: 16 KB; Date recorded: Sep. 29, 2020).

BACKGROUND

Technical Field

The present invention relates to an agricultural or horticultural composition.

Background Art

*Bacillus amyloliquefaciens* is a bacterium present in soil, and has been reported to settle in the rhizosphere of plants. Furthermore, as *Bacillus amyloliquefaciens*, a plurality of strains showing an action of promoting growth of plants, such as the FZB42 strain, have been isolated. The FZB42 strain has been the most studied for interaction with plants among *Bacillus amyloliquefaciens* strains (Chowdhury S P et al., Biocontrol mechanism by root-associated *Bacillus amyloliquefaciens* FZB42—a review. Front Microbiol. 2015 Jul. 28; 6:780), and is commercially available as a microbial material (product name: RhizoVital42). In addition, it has been reported that the plant-growth-promoting action of the FZB42 strain relates to production of indole-3-acetic acid (IAA), and that the plant-growth-promoting action is decreased due to deletion of IAA biosynthesis genes (Idris E E et al., Tryptophan-dependent production of indole-3-acetic acid (IAA) affects level of plant growth promotion by *Bacillus amyloliquefaciens* FZB42. Mol Plant Microbe Interact. 2007 June; 20(6):619-26).

Prephenate dehydratase (PD) is one of the phenylalanine biosynthesis enzymes. PD is known to typically be subject to feedback inhibition by phenylalanine. Furthermore, various mutations that reduce or eliminate feedback inhibition by phenylalanine are known for PD. PD in which feedback inhibition by phenylalanine was reduced or eliminated is used for, for example, fermentative production of phenylalanine.

SUMMARY

Provided is an agricultural or horticultural composition. Application of a culture broth of a *Bacillus* bacterium having prephenate dehydratase (PD) resistant to feedback inhibition by phenylalanine to a plant has been found to improve growth of the plant.

It is an aspect of the present invention to provide an agricultural or horticultural composition, the composition comprising a culture broth of a *Bacillus* bacterium having prephenate dehydratase resistant to feedback inhibition by phenylalanine.

It is a further aspect to provide the composition as described above, wherein the *Bacillus* bacterium is *Bacillus amyloliquefaciens* or *Bacillus velezensis*.

It is a further aspect of the present invention to provide the composition as described above, wherein the culture broth is the culture broth of the *Bacillus* bacterium, a culture supernatant separated from the culture broth, or a processed product thereof.

It is a further aspect of the present invention to provide the composition as described above, wherein the processed product is a product subjected to condensation, dilution, fractionation, sterilization, or a combination thereof.

It is a further aspect of the present invention to provide the composition as described above, which is a composition that is able to promote growth of a plant.

It is a further aspect of the present invention to provide the composition as described above, wherein the prephenate dehydratase has a mutation at a position, relative to the wild-type prephenate dehydratase, selected from the group consisting of A)S213, B) N229, C) F247, and combinations thereof.

It is a further aspect of the present invention to provide the composition as described above, wherein the mutation is selected from the group consisting of A) S213L, B) N229Y, C) F247Y, and D) combinations thereof.

It is a further aspect of the present invention to provide the composition as described above, wherein the wild-type prephenate dehydratase is selected from the group consisting of (a) a protein comprising the amino acid sequence of SEQ ID NO: 2 or 4; (b) a protein comprising the amino acid sequence of SEQ ID NO: 2 or 4, but which includes substitution, deletion, insertion, and/or addition of 1 to 10 amino acid residues; and (c) a protein comprising an amino acid sequence having an identity of 90% or higher to the amino acid sequence of SEQ ID NO: 2 or 4.

It is a further aspect of the present invention to provide a method for promoting growth of a plant, the method comprising applying a culture broth of a *Bacillus* bacterium having prephenate dehydratase resistant to feedback inhibition by phenylalanine to the plant.

It is a further aspect of the present invention to provide a method for producing a plant body, the method comprising applying a culture broth of a *Bacillus* bacterium having prephenate dehydratase resistant to feedback inhibition by phenylalanine to a plant to cultivate the plant; and collecting the plant body.

It is a further aspect of the present invention to provide the method as described above, wherein the *Bacillus* bacterium is *Bacillus amyloliquefaciens* or *Bacillus velezensis*.

It is a further aspect of the present invention to provide the method as described above, wherein the culture broth is the culture broth of the *Bacillus* bacterium, a culture supernatant separated from the culture broth, or a processed product thereof.

It is a further aspect of the present invention to provide the method as described above, wherein the processed product is a product subjected to condensation, dilution, fractionation, sterilization, or a combination thereof.

It is a further aspect of the present invention to provide the method as described above, wherein the culture broth is applied to soil or a medium.

It is a further aspect of the present invention to provide the method as described above, wherein the culture broth is applied in an amount of 1 L/ha to 10000 L/ha immediately after completion of the culture.

It is a further aspect of the present invention to provide the method as described above, wherein the culture broth is applied so that the concentration of the culture broth in the rhizosphere of the plant is 0.01% (w/w) to 150% (w/w) immediately after completion of the culture.

It is a further aspect of the present invention to provide the method as described above, wherein the prephenate dehydratase has a mutation at a position, relative to a wild-type prephenate dehydratase, selected from the group consisting of A) S213, B) N229, C) F247, and D) combinations thereof.

It is a further aspect of the present invention to provide the composition as described above, wherein the mutation is selected from the group consisting of A) S213L, B) N229Y, C) F247Y, and D) combinations thereof.

It is a further aspect of the present invention to provide the method as described above, wherein the wild-type prephenate dehydratase is selected from the group consisting of (a) a protein comprising the amino acid sequence of SEQ ID NO: 2 or 4; (b) a protein comprising the amino acid sequence of SEQ ID NO: 2 or 4, but which includes substitution, deletion, insertion, and/or addition of 1 to 10 amino acid residues; and (c) a protein comprising an amino acid sequence having an identity of 90% or higher to the amino acid sequence of SEQ ID NO: 2 or 4.

BRIEF DESCRIPTION OF THE DRAWINGS

FIG. 1 is a graph showing the effect of increasing the number of lateral roots of *Arabidopsis thaliana* provided by a culture broth of a *Bacillus* bacterium having prephenate dehydratase (PD) resistant to feedback inhibition by phenylalanine.

DETAILED DESCRIPTION

A culture broth of a *Bacillus* bacterium having prephenate dehydratase (PD) resistant to feedback inhibition by phenylalanine is described. This culture broth can also be referred to as an "active ingredient" or a "culture broth as described herein". This *Bacillus* bacterium is also referred to as "bacterium as described herein".

By using the active ingredient, specifically, by applying the active ingredient to a plant, growth of the plant can be promoted, that is, an effect of promoting growth of the plant can be obtained. This effect is also referred to as "growth-promoting effect". Examples of the promotion of growth include promotion of root formation. Examples of the promotion of root formation include an increase in the number of lateral roots and increase in the weight of underground part.

The growth-promoting effect can be confirmed on the basis of, for example, growth of the plant as an indicator. That is, if growth of the plant is improved when using the active ingredient as compared to when not using the active ingredient, it can be judged that the growth-promoting effect was obtained.

<1>Plant

The kind of plant is not particularly limited. The plant may be a woody plant, or may be an herbaceous plant. Examples of the plant include plants of the family Poaceae (*Gramineae*) (rice, barley, wheat, corn, oats, turf grass, etc.), plants of the family Solanaceae (tomato, green pepper, eggplant, potato, etc.), plants of the family Cucurbitaceae (cucumber, melon, pumpkin, etc.), plants of the family Fabaceae (Leguminosae) (pea, soybean, kidney bean, alfalfa, peanut, fava bean, etc.), plants of the family Brassicaceae (radish, cabbage, Chinese cabbage, Japanese mustard spinach, canola flower, bok-choy, *Arabidopsis thaliana*, etc.), plants of the family Rosaceae (strawberry, apple, pear, etc.), plants of the family Moraceae plant (mulberry, etc.), plants of the family Malvaceae (cotton, etc.), plants of the family Apiaceae (carrot, parsley, celery, etc.), plants of the family Liliaceae (green onion, onion, asparagus, etc.), plants of the family Asteraceae (burdock, sunflower, *chrysanthemum*, crown daisy, safflower, lettuce, etc.), plants of the family Ericaceae (blueberry, etc.), plants of the family Vitaceae (grape, etc.), and plants of the family Rutaceae (mandarin orange, lemon, Yuzu, etc.). Particular examples of the plant include plants of the family Solanaceae, Cucurbitaceae, and Rosaceae. More particular examples of the plant include tomato, cucumber, and strawberry. As the plant, one kind of plant can be employed as the target, or two or more kinds of plants can be employed as the target.

<2>Active Ingredient and Production Thereof

The active ingredient (i.e. the culture broth as described herein) can be obtained by culturing the bacterium as described herein. That is, a method is described for producing the active ingredient, the method including a step of culturing the bacterium as described herein in a medium. This step is also referred to as "cultivation step". The cultivation step may specifically be a step of culturing the bacterium in a medium to thereby prepare the active ingredient.

As described below, the active ingredient can be used as an active ingredient in an agricultural or horticultural composition, such as a growth-promoting agent for a plant. That is, the method for producing the active ingredient may also be read as a method for producing an agricultural or horticultural composition, such as a method for producing a growth-promoting agent for a plant.

<2-1>Bacterium

The bacterium is a *Bacillus* bacterium having PD resistant to feedback inhibition by phenylalanine.

Incidentally, the bacterium or a bacterium used for constructing the same is also referred to as "host".

<2-1-1>*Bacillus* Bacteria

Examples of the *Bacillus* bacterium include, for example, *Bacillus subtilis*, *Bacillus amyloliquefaciens*, *Bacillus pumilus*, *Bacillus lichenifonnis*, *Bacillus megaterium*, *Bacillus brevis*, *Bacillus polymixa*, *Bacillus stearothermophilus*, and *Bacillus velezensis*. Particular examples of the *Bacillus* bacterium include *Bacillus amyloliquefaciens* and *Bacillus velezensis*. Specific examples of *Bacillus subtilis* include, for example, 168 Marburg strain (ATCC 6051), PY79 strain (Plasmid, 1984, 12, 1-9), and derivative strains thereof. Specific examples of *Bacillus amyloliquefaciens* include, for example, T strain (ATCC 23842), N strain (ATCC 23845), AJ11708 strain (NITE BP-02609), FZB42 strain (DSM 23117), and derivative strains thereof. Incidentally, the FZB42 strain (DSM 23117) was proposed to be re-classified into *Bacillus velezensis* (Dunlap C A, et al., *Bacillus velezensis* is not a later heterotypic synonym of *Bacillus amyloliquefaciens*; *Bacillus methylotrophicus*, *Bacillus amyloliquefaciens* subsp *plantarum* and '*Bacillus oryzicola*' are later heterotypic synonyms of *Bacillus velezensis* based on phylogenomics. Int. J. Syst. Evol. Microbiol. (2016), 66, 1212-1217). Hence, although the FZB42 strain (DSM 23117) is described as *Bacillus amyloliquefaciens* for convenience of explanation, it should be recognized to fall within both *Bacillus amyloliquefaciens* and *Bacillus velezensis*. That is, specific examples of *Bacillus velezensis* include, for example, the FZB42 strain (DSM 23117) and derivative strains thereof.

Furthermore, examples of the *Bacillus* bacterium also include, for example, strains of which the nucleotide sequence of the 16S rRNA gene has an identity of 99% or more, 99.5% or more, 99.7% or more, 99.86% or more, 99.93% or more, or 100% with respect to that of the AJ11708 strain (NI IE BP-02609) or the FZB42 strain (DSM 23117). Such strains each may be classified as, for example, *Bacillus amyloliquefaciens* or *Bacillus velezensis*.

These strains are available from, for example, the American Type Culture Collection (Address: 10801 University Boulevard, Manassas, VA 20108, United States of America). That is, registration numbers are given to the respective strains, and the strains can be ordered by using these registration numbers (refer to atcc.org). The registration numbers of the strains are listed in the catalogue of the American Type Culture Collection. These strains can also be obtained from, for example, Leibniz Institute DSMZ-German Collection of Microorganisms and Cell Cultures (Address: Inhoffenstrasse 7B 38124 Braunschweig, GERMANY). These strains can also be obtained from, for example, the depositories at which the strains were deposited.

<2-1-2>Inhibition-Resistant Prephenate Dehydratase

The term "prephenate dehydratase (PD)" refers to a protein having an activity of catalyzing the reaction of converting prephenate to phenylpyruvate. This activity can also be referred to as "prephenate dehydratase activity (PD activity)". A gene encoding PD can also be referred to as "prephenate dehydratase gene (PD gene)".

PD is known to typically be subject to feedback inhibition by phenylalanine. PD resistant to feedback inhibition by phenylalanine is also referred to as "inhibition-resistant prephenate dehydratase (inhibition-resistant PD)". A gene encoding the inhibition-resistant PD is also referred to as "inhibition-resistant prephenate dehydratase gene (inhibition-resistant PD gene)". PD not resistant to feedback inhibition by phenylalanine is also referred to as "wild-type prephenate dehydratase (wild-type PD)". A gene encoding the wild-type PD is also referred to as "wild-type prephenate dehydratase gene (wild-type PD gene)". The wild-type PD can be modified to be the inhibition-resistant PD by introduction of a mutation of reducing or eliminating feedback inhibition by phenylalanine. This mutation is also referred to as "inhibition-resistant mutation". In addition, for the inhibition-resistant PD gene, a mutation on the nucleotide sequence thereof resulting in the inhibition-resistant mutation on the encoded PD is also referred to as "inhibition-resistant mutation". The term "wild-type" referred to herein is used for convenience for distinguishing "wild-type" genes from "inhibition-resistant" genes, and the wild-type gene or enzyme is not limited to a naturally occurring one, so long as the gene or enzyme does not have the inhibition-resistant mutation. Each inhibition-resistant PD may have or may not have the corresponding wild-type PD.

Examples of the wild-type PD include PDs of various organisms. The nucleotide sequence of the wild-type PD gene (pheA gene) of *Bacillus amyloliquefaciens* AJ11708 and the amino acid sequence of the wild-type PD (PheA) encoded by this gene are shown as SEQ ID NOS: 1 and 2, respectively. The nucleotide sequence of the wild-type PD gene (pheA gene) of *Bacillus amyloliquefaciens* FZB42 and the amino acid sequence of the wild-type PD (PheA) encoded by this gene are shown as SEQ ID NOS: 3 and 4, respectively. The nucleotide sequence of the wild-type PD gene (pheA gene) of *Escherichia coli* K-12 MG1655 and the amino acid sequence of the wild-type PD (PheA) encoded by this gene are shown as SEQ ID NOS: 5 and 6, respectively. The PheA of *Escherichia coli* is encoded by the pheA gene as a bifunctional enzyme, chorismate mutase-prephenate dehydratase (CM-PD). The nucleotide sequence of the wild-type PD gene of *Brevibacterium lactofermentum* AJ12125 (FERM P-7546) and the amino acid sequence of the wild-type PD encoded by this gene are shown as SEQ ID NOS: 7 and 8, respectively. That is, the wild-type PD may be, for example, a protein encoded by a gene having the nucleotide sequence shown as SEQ ID NO: 1, 3, 5, or 7. Also, the wild-type PD may be, for example, a protein having the amino acid sequence shown as SEQ ID NO: 2, 4, 6, or 8. The expression "a gene or protein has a nucleotide or amino acid sequence" means that a gene or protein can include the nucleotide or amino acid sequence among other sequences unless otherwise stated, and also can mean that the gene or protein consists of only the nucleotide or amino acid sequence as described herein.

The wild-type PD may be a variant of any of the wild-type PDs exemplified above (e.g. a protein having the amino acid sequence shown as SEQ ID NO: 2, 4, 6, or 8), so long as it does not have the inhibition-resistant mutation. That is, the wild-type PD may have a mutation other than the inhibition-resistant mutation, so long as it does not have the inhibition-resistant mutation. Examples of the variant include, for example, homologues and artificially modified versions of any of the wild-type PDs exemplified above. Examples of such homologues include PD homologues of other microorganisms, of which structure is similar to that of any of the wild-type PDs exemplified above. PD homologues of other microorganisms can be obtained from, for example, a public database by BLAST search and FASTA search using the amino acid sequence of any of the wild-type PDs exemplified above as a query sequence.

The wild-type PD typically has PD activity. However, the wild-type PD may have or may not have PD activity, so long as the corresponding inhibition-resistant PD has PD activity.

PD activity can be measured by, for example, incubating an enzyme with a substrate (i.e. prephenate), and measuring the enzyme- and substrate-dependent generation of product (i.e. phenylpyruvate). Generation of product can be confirmed by known methods used for detection or identification of compounds, such as HPLC, UPLC, GC/MS, and NMR.

The wild-type PD may be a protein having the amino acid sequence of any of the wild-type PDs exemplified above (for example, the amino acid sequence shown as SEQ ID NO: 2, 4, 6, or 8), but including substitution, deletion, insertion, and/or addition of one or several amino acid residues at one or several positions, so long as it does not have the inhibition-resistant mutation. Although the number meant by the term "one or several" can differ depending on the positions of amino acid residues in the three-dimensional structure of the protein, or the types of amino acid residues, specifically, it is, for example, 1 to 50, 1 to 40, or 1 to 30, 1 to 20, 1 to 10, 1 to 5, or 1 to 3.

The aforementioned substitution, deletion, insertion, or addition of one or several amino acid residues may be a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, or addition of amino acid residues as mentioned above includes a naturally occurring mutation (mutant or variant), such as those due to a difference of individuals or species of the organism from which the gene is derived.

The wild-type PD may be a protein having an amino acid sequence showing a homology of 80% or higher, 90% or higher, 95% or higher, 97% or higher, or 99% or higher, to the amino acid sequence of any of the wild-type PDs exemplified above (for example, the amino acid sequence shown as SEQ ID NO: 2, 4, 6, or 8), so long as it does not have the inhibition-resistant mutation. In this description, "homology" means "identity".

The wild-type PD may be a protein encoded by a gene, such as DNA, that is able to hybridize under stringent conditions with a probe that can be prepared from the nucleotide sequence of any of the wild-type PD genes exemplified above (for example, the nucleotide sequence shown as SEQ ID NO: 1, 3, 5, or 7), such as a probe having a sequence complementary to a part or the whole of the nucleotide sequence of any of the wild-type PD genes exemplified above (for example, the nucleotide sequence shown as SEQ ID NO: 1, 3, 5, or 7), so long as it does not have the inhibition-resistant mutation. Such a probe can be prepared by PCR using oligonucleotides produced on the basis of a known wild-type PD gene sequence as primers, and a DNA fragment containing the nucleotide sequence of the wild-type PD gene as the template. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C. Furthermore, for example, when a DNA fragment having a length of about 300 bp is used as the probe, the washing conditions of the hybridization can be, for example, 50° C., 2×SSC, and 0.1% SDS. Those skilled in the art can realize stringency equivalent to the stringency of the hybridization exemplified above by determining various conditions such as salt concentrations and temperature.

Furthermore, in the wild-type PD gene, any codons may be replaced with equivalent codons, so long as it encodes the wild-type PD. That is, the wild-type PD gene may be a variant of any of the wild-type PD genes exemplified above due to the degeneracy of the genetic code. For example, in the wild-type PD gene, codons may be optimized according to codon frequencies observed in the chosen host.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and a modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program include, but not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244, Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST (BLAST 2.0) can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other. The term "identity" between amino acid sequences may specifically mean an identity calculated by blastp with default scoring parameters (i.e. Matrix, BLOSUM62; Gap Costs, Existence=11, Extension=1; Compositional Adjustments, Conditional compositional score matrix adjustment), unless otherwise stated. The term "identity" between nucleotide sequences may specifically mean an identity calculated by blastn with default scoring parameters (i.e. Match/Mismatch Scores=1, −2; Gap Costs=Linear), unless otherwise stated.

Hereinafter, the inhibition-resistant PD will be explained.

The inhibition-resistant PD is a protein that has PD activity and is resistant to feedback inhibition by phenylalanine. The phrase "resistant to feedback inhibition by phenylalanine" means that the protein exhibits PD activity in the presence of L-phenylalanine. The phrase "resistant to feedback inhibition by phenylalanine" may specifically mean that PD activity in the presence of 0.5 mM, 1 mM, 5 mM, or 10 mM of L-phenylalanine is 50% or higher, 70% or higher, or 90% or higher of PD activity in the absence of L-phenylalanine.

The inhibition-resistant PD may be, for example, a protein having the inhibition-resistant mutation in the amino acid sequence of the wild-type PD.

That is, for example, the inhibition-resistant PD may be a protein having the amino acid sequence shown as SEQ ID NO: 2, 4, 6, or 8, but including the inhibition-resistant mutation. The inhibition-resistant PD may also be, for example, a protein having the amino acid sequence shown as SEQ ID NO: 2, 4, 6, or 8, but including the inhibition-resistant mutation, further including substitution, deletion, insertion, and/or addition of one or several amino acid residues at a site other than that of the inhibition-resistant mutation, and having PD activity.

In other words, the inhibition-resistant PD may be a protein having an amino acid sequence identical to that of the wild-type PD, except that it has the inhibition-resistant mutation. For example, the inhibition-resistant PD may be a protein having the amino acid sequence shown as SEQ ID NO: 2, 4, 6, or 8, except that it has the inhibition-resistant mutation. The inhibition-resistant PD may also be, for example, a protein having the amino acid sequence shown as SEQ ID NO: 2, 4, 6, or 8, but including substitution, deletion, insertion, and/or addition of one or several amino acid residues, and having PD activity, except that it has the inhibition-resistant mutation. The inhibition-resistant PD may also be, for example, a protein having an amino acid sequence having a homology of 80% or higher, 90% or higher, 95% or higher, 97% or higher, or 99% or higher, to the amino acid sequence shown as SEQ ID NO: 2, 4, 6, or 8, and having PD activity, except that it has the inhibition-resistant mutation.

The inhibition-resistant PD gene is not particularly limited so long as it encodes such an inhibition-resistant PD as mentioned above. The term "gene" is not limited to DNA, but may include any polynucleotide, so long as it encodes a target protein. That is, the term "inhibition-resistant PD gene" may mean any polynucleotide encoding the inhibition-resistant PD. The inhibition-resistant PD gene may be DNA, RNA, or a combination thereof. The inhibition-resistant PD gene may be single-stranded or double-stranded. The inhibition-resistant PD gene may be a single-stranded DNA or a single-stranded RNA. The inhibition-resistant PD gene may be a double-stranded DNA, a double-stranded RNA, or a hybrid strand consisting of a DNA strand and an RNA strand. The inhibition-resistant PD gene may contain both a DNA residue and an RNA residue in a single polynucleotide chain. When the inhibition-resistant PD gene contains RNA, the aforementioned descriptions concerning DNA, such as those concerning nucleotide sequences exemplified above, may be applied to RNA with appropriately changing wordings to those for RNA as required. The mode of the inhibition-resistant PD gene can be chosen according to various conditions such as use thereof.

Hereinafter, the inhibition-resistant mutation will be explained.

Examples of the inhibition-resistant mutation include a mutation corresponding to a mutation at one or more of the following amino acid residues:

S213, N229, F247.

In the aforementioned description, the numerals indicate the positions in the amino acid sequence of the wild-type PD shown as SEQ ID NO: 2, and the letters on the left side of the numerals indicate the amino acid residues at the respective positions in the amino acid sequence of the wild-type PD shown as SEQ ID NO: 2 (namely, the amino acid residues before being mutated, indicated with one-letter code). For example, "S213" indicates the Ser residue at position 213 in the amino acid sequence of the wild-type PD shown as SEQ ID NO: 2.

As for the aforementioned mutation, the amino acid residues after substitution may be any amino acid residues other than the original amino acid residues, so long as the inhibition-resistant PD can be obtained. Specific examples of the amino acid residue after the substitution include K (Lys), R (Arg), H (His), A (Ala), V (Val), L (Leu), I (Ile), G (Gly), S (Ser), T (Thr), P (Pro), F (Phe), W (Trp), Y (Tyr), C (Cys), M (Met), D (Asp), E (Glu), N (Asn), and Q (Gln), which should be other than the original amino acid residues.

Specific examples of the inhibition-resistant mutation include a mutation corresponding to one or more of the following mutations. That is, the inhibition-resistant mutation may include a mutation corresponding to one or more of the following mutations. The inhibition-resistant mutation may be, for example, a mutation corresponding to any one of the following mutation, or may be a mutation corresponding to a combination of two or more of the following mutations. The combination of the mutations is not particularly limited:

S213L, N229Y, F247Y.

In the aforementioned descriptions, the meanings of the numerals and the letters on the left side of the numerals are the same as those described above. The letters in the parentheses on the right side of the numerals indicate the amino acid residues (one-letter code) after being mutated. That is, for example, "S213L" means a mutation that the Ser residue at position 213 in the amino acid sequence of the wild-type PD shown as SEQ ID NO: 2 is replaced with a Leu residue.

The term "a mutation corresponding to a mutation of an amino acid residue at position n in the amino acid sequence shown as SEQ ID NO: 2" in the amino acid sequence of any chosen wild-type PD means a mutation at an amino acid residue corresponding to the amino acid residue at position n in the amino acid sequence shown as SEQ ID NO: 2. That is, for example, the term "a mutation corresponding to S213L" refers to a mutation that an amino acid residue corresponding to the Ser residue at position 213 (S213) in the amino acid sequence of wild-type PD shown as SEQ ID NO: 2 is replaced with a Leu residue. The "amino acid residue corresponding to S213" mentioned here may typically be a Ser residue, but may not be a Ser residue. Namely, for example, the term "a mutation corresponding to S213L" is not limited to a mutation that when the "amino acid residue corresponding to S213" is a Ser residue, the Ser residue is replaced with a Leu residue, but includes a mutation that when the "amino acid residue corresponding to S213" is Lys, Arg, His, Ala, Val, Ile, Gly, Thr, Pro, Phe, Trp, Tyr, Cys, Met, Asp, Glu, Asn, or Gln residue, this amino acid residue is replaced with a Leu residue. The same shall apply to the other mutations.

The term "an amino acid residue corresponding to the amino acid residue at position n in the amino acid sequence shown as SEQ ID NO: 2" in the amino acid sequence of any chosen wild-type PD means an amino acid residue corresponding to the amino acid residue at position n in the amino acid sequence shown as SEQ ID NO: 2 in an alignment of the target amino acid sequence of wild-type PD and the amino acid sequence of SEQ ID NO: 2. That is, as for the aforementioned mutation, the position of amino acid residue does not necessarily indicate an absolute position in the amino acid sequence of a wild-type PD, but indicates a relative position based on the amino acid sequence shown as SEQ ID NO: 2. For example, when one amino acid residue is deleted at a position on the N-terminus side of position n in the wild-type PD consisting of the amino acid sequence shown as SEQ ID NO: 2, the amino acid residue originally at position n becomes the (n−1)$^{th}$ amino acid residue counted from the N-terminus, but it is regarded as the "amino acid residue corresponding to the amino acid residue at position n in the amino acid sequence shown as SEQ ID NO: 2". Similarly, for example, when the amino acid residue at position 100 in the amino acid sequence of a PD homologue of a certain microorganism corresponds to position 101 of the amino acid sequence shown as SEQ ID NO: 2, this amino acid residue is the "amino acid residue corresponding to the amino acid residue at position 101 in the amino acid sequence shown as SEQ ID NO: 2" in the PD homologue.

Such alignment can be performed by, for example, using known gene analysis software. Specific examples of such software include DNASIS produced by Hitachi Solutions, GENETYX produced by Genetyx, ClustalW opened to the public by DDBJ, and so forth (Elizabeth C. Tyler et al., Computers and Biomedical Research, 24(1), 72-96, 1991; Barton G. J. et al., Journal of Molecular Biology, 198 (2), 327-37, 1987; Thompson J D et al., Nucleic Acid Research, 22 (22), 4673-80, 1994).

Examples of the inhibition-resistant mutation also include a mutation wherein an amino acid residue corresponding to the Ser residue at position 330 of SEQ ID NO: 6 is replaced with another amino acid residue in a wild-type PD (Japanese Patent Laid-open (Kokai) No. 5-76352). Examples of the other amino acid residue include Pro residue and Asp residue. Particular examples of the other amino acid residue include Pro residue.

Examples of the inhibition-resistant mutation also include a mutation that amino acid residues from an amino acid residue corresponding to the Trp residue at position 338 of SEQ ID NO: 6 to the C-terminal amino acid residue are deleted or replaced with one or several amino acid residues in a wild-type PD (Japanese Patent Laid-open (Kokai) No. 1-235597 and WO87/00202). The number meant by the term "one or several" may be, for example, 1, 2, 3, 4, or 5. Examples of the one or several amino acid residues include Arg-Gly and Trp-Arg-Ser-Pro.

The positions of amino acid residues of these mutations in any chosen wild-type PD can also be determined on the basis of an alignment with SEQ ID NO: 6, as with "an amino acid residue corresponding to the amino acid residue at position n in the amino acid sequence shown as SEQ ID NO: 2". For example, the Ser residue at position 330 of SEQ ID NO: 6 corresponds to the Ser residue at position 235 of SEQ ID NO: 8.

The inhibition-resistant PD gene can be obtained by, for example, modifying the wild-type PD gene so that the encoded protein has the inhibition-resistant mutation. The wild-type PD gene to be modified can be obtained by, for example, cloning from an organism having the wild-type PD gene, or chemical synthesis. Furthermore, the inhibition-resistant PD gene can also be obtained without using the wild-type PD gene. For example, the inhibition-resistant PD gene may be directly obtained by chemical synthesis. The obtained inhibition-resistant PD gene may be used as it is, or may be appropriately modified before use. For example, an inhibition-resistant PD gene may be modified to obtain another inhibition-resistant PD gene. The inhibition-resistant PD gene or the wild-type PD gene may be a gene derived from the host, or may be a heterologous gene.

Modification of a gene can be performed by a known method. For example, by the site-specific mutagenesis method, an objective mutation can be introduced into a target site of DNA. Examples of the site-specific mutagenesis method include a method of using PCR (Higuchi, R., 61, in PCR Technology, Erlich, H. A. Eds., Stockton Press, 1989; Carter P., Meth., in Enzymol., 154, 382, 1987), and a method of using a phage (Kramer, W and Frits, H. J., Meth. in Enzymol., 154, 350, 1987; Kunkel, T. A. et al., Meth. in Enzymol., 154, 367, 1987).

The inhibition-resistant PD is expressed from the inhibition-resistant PD gene. Hence, the bacterium as described herein has the inhibition-resistant PD gene. Specifically, the bacterium has the inhibition-resistant PD gene so that the gene can be expressed. The bacterium may inherently have the inhibition-resistant PD gene, or may have been modified so as to have the inhibition-resistant PD gene. A *Bacillus* bacterium having the inhibition-resistant PD gene can be obtained by introducing the inhibition-resistant PD gene into such a *Bacillus* bacterium as mentioned above. That is, the bacterium may be a modified strain derived from such a *Bacillus* bacterium as mentioned above. Specific examples of the bacterium include *Bacillus amyloliquefaciens* AJ111345 (NITE BP-02610). Incidentally, the phrase "introducing the inhibition-resistant PD gene into a *Bacillus* bacterium" also includes modifying a PD gene on the chromosome of the *Bacillus* bacterium to the inhibition-resistant PD gene, e.g. introducing the inhibition-resistant mutation into a PD gene on the chromosome of the *Bacillus* bacterium.

The method for introducing the inhibition-resistant PD gene into the host is not particularly limited. In the host, the inhibition-resistant PD gene may be harbored in such a manner that it can be expressed under control of a promoter that functions in the host. In the host, the inhibition-resistant PD gene may exist on a vector autonomously replicable out of the chromosome such as plasmid, or may be introduced into the chromosome. The host may have only one copy of the inhibition-resistant PD gene, or may have two or more copies of the inhibition-resistant PD gene. The host may have only one kind of inhibition-resistant PD gene, or may have two or more kinds of inhibition-resistant PD genes.

The promoter for expressing the inhibition-resistant PD gene is not particularly limited so long as it is a promoter that functions in the host. The "promoter that functions in a host" refers to a promoter that shows a promoter activity in the host. The promoter may be a promoter derived from the host, or a heterologous promoter. The promoter may be the native promoter of the PD gene, or may be a promoter of another gene. The promoter may be a promoter stronger than the native promoter of the PD gene. Examples of promoters that function in *Bacillus* bacteria include veg promoter, spac promoter, xyl promoter, and groESL promoter. Furthermore, as the promoter, a highly-active type of an existing promoter may also be obtained by using various reporter genes. For example, by making the −35 and −10 regions in a promoter region closer to the consensus sequence, the activity of the promoter can be enhanced (WO00/18935). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

Also, a terminator for termination of gene transcription may be located downstream of the inhibition-resistant PD gene. The terminator is not particularly limited so long as it functions in the bacterium. The terminator may be a terminator derived from the host, or a heterogenous terminator. The terminator may be the native terminator of the PD gene, or a terminator of another gene.

The inhibition-resistant PD gene can be introduced into the host, for example, by using a vector containing the gene. A vector containing the inhibition-resistant PD gene is also referred to as "expression vector for the inhibition-resistant PD gene". The expression vector for the inhibition-resistant PD gene can be constructed by, for example, ligating a DNA fragment containing the inhibition-resistant PD gene with a vector that functions in the host. By transforming the host with the expression vector for the inhibition-resistant PD gene, a transformant into which the vector has been introduced is obtained, i.e. the gene can be introduced into the host. As the vector, a vector autonomously replicable in the cell of the host can be used. The vector can be a multi-copy vector. Furthermore, the vector can have a marker such as an antibiotic resistance gene or an auxotrophy complimenting gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in *Bacillus* bacteria include, for example, pUB110, pC194, and pE194. For constructing the expression vector, for example, the inhibition-resistant PD gene having a native promoter region as it is may be incorporated into a vector, a coding region of the inhibition-resistant PD ligated downstream from such a promoter as mentioned above may be incorporated into a vector, or a coding region of the inhibition-resistant PD may be incorporated into a vector downstream from a promoter originally existing in the vector.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

The inhibition-resistant PD gene can also be introduced into, for example, the chromosome of the host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination include, for example, a method of using a linear DNA, a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for carrying out the present invention as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1). For introducing the inhibition-resistant PD gene into a chromosome, for example, the inhibition-resistant PD gene having a native promoter region as it is may be incorporated into the chromosome, a coding region for the inhibition-resistant PD ligated downstream from such a promoter as mentioned above may be incorporated into the chromosome, or a coding region for the inhibition-resistant PD may be incorporated into the chromosome downstream from a promoter originally present in the chromosome.

Introduction of a gene into a chromosome can be confirmed by, for example, Southern hybridization using a probe having a nucleotide sequence complementary to a part or the whole of the gene, or PCR using primers prepared on the basis of the nucleotide sequence of the gene.

The method for transformation is not particularly limited, and generally used methods, such as the protoplast method (Gene, 39, 281-286(1985)), the electroporation method (Bio/Technology, 7, 1067-1070(1989)), and the electric pulse method (Japanese Patent Laid-open (Kokai) No. 2-207791), can be used.

In addition, introduction of the inhibition-resistant mutation into the PD gene on the chromosome can also be attained by, for example, natural mutation or mutagenesis treatment. A strain of which the PD gene on the chromosome has been introduced with the inhibition-resistant mutation can be obtained, for example, as a phenylalanine analogue resistant strain. Examples of the phenylalanine analogue include p-fluorophenylalanine (f-Phe).

The bacterium may have or may not have the wild-type PD gene. A host not having the wild-type PD gene can be obtained by disrupting the wild-type PD gene on the chromosome. For example, a host not having the wild-type PD gene but having the inhibition-resistant PD gene can be obtained by replacing the wild-type PD gene on the chromosome with the inhibition-resistant PD gene.

<2-2>Production of the Active Ingredient

The active ingredient (i.e. the culture broth as described herein) can be obtained by culturing the bacterium as described herein.

The medium to be used is not particularly limited, so long as the chosen bacterium can proliferate in it. As the medium, for example, a usual medium used for culture of bacteria such as *Bacillus* bacteria can be used. As the medium, for example, a medium containing a carbon source, nitrogen source, phosphorus source, and sulfur source, as well as components selected from other various organic components and inorganic components as required can be used. The types and concentrations of medium components can be appropriately set by a skilled artisan according to various conditions such as the type of bacterium to be used. For a specific medium composition, for example, the medium compositions described in previous reports regarding methods for producing substances such as purine substances by bacteria such as *Bacillus* bacteria (e.g. Japanese Patent Laid-open (Kokai) No. 2015-029474 and 2007-117078) can be used as a reference.

The carbon source is not particularly limited, so long as the bacterium can utilize it. Specific examples of the carbon source include, for example, saccharides such as glucose, fructose, sucrose, lactose, galactose, xylose, arabinose, blackstrap molasses, hydrolysates of starches, and hydrolysates of biomass, organic acids such as acetic acid, fumaric acid, citric acid, and succinic acid, alcohols such as glycerol, crude glycerol, and ethanol, and aliphatic acids. As the carbon source, a single kind of carbon source may be used, or two or more kinds of carbon sources may be used in combination.

Specific examples of the nitrogen source include, for example, ammonium salts such as ammonium sulfate, ammonium chloride, and ammonium phosphate, organic nitrogen sources such as peptone, yeast extract, meat extract, corn steep liquor, and soybean protein decomposition products, ammonia, and urea. As the nitrogen source, a single kind of nitrogen source may be used, or two or more kinds of nitrogen sources may be used in combination.

Specific examples of the phosphate source include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

The culture conditions are not particularly limited so long as the bacterium can proliferate. The culture can be performed, for example, under usual conditions used for culturing bacteria such as Bacillus bacteria. The culture conditions can be appropriately set by a skilled artisan according to various conditions such as the type of chosen bacterium. For specific culture conditions, for example, the culture conditions described in previous reports regarding methods for producing substances such as purine substances by bacteria such as Bacillus bacteria (e.g. Japanese Patent Laid-open (Kokai) No. 2015-029474 and 2007-117078) can be used as a reference.

The culture can be performed, for example, under an aerobic condition by using a liquid medium. Specifically, the culture under an aerobic condition can be performed by aeration culture, shaking culture, stirring culture, or a combination thereof. The pH of the medium may be, for example, 3 to 10, or 4.0 to 9.5. During the culture, the pH of the medium can be adjusted as required. The pH of the medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 15 to 43° C., 25 to 37° C., or about 34° C. The culture period, for example, may be 10 hours or longer, 15 hours or longer, 20 hours or longer, 30 hours or longer, 50 hours or longer, or 70 hours or longer, may be 240 hours or shorter, 180 hours or shorter, 120 hours or shorter, 90 hours or shorter, 70 hours or shorter, or 50 hours or shorter, or may be within a range defined as a non-contradictory combination thereof. The culture period may specifically be, for example, 10 to 120 hours. Furthermore, when using an inducible promoter for expression of the inhibition-resistant PD, the expression of the inhibition-resistant PD can be appropriately induced. The culture can be performed as batch culture, fed-batch culture, continuous culture, or a combination of these. Furthermore, the culture can be performed separately as seed culture and main culture. For example, the seed culture may be performed on a solid medium, and the main culture may be performed in a liquid medium. The culture may be continued, for example, until the carbon source contained in the medium is consumed, or until the bacterium as described herein loses the activity.

By culturing the bacterium under such conditions as described above, a culture broth of the bacterium can be obtained.

The culture broth may be used as the active ingredient as it is, or may be used as the active ingredient after being appropriately subjected to a treatment such as condensation, dilution, fractionation, and sterilization. These treatments are not particularly limited, so long as the growth-promoting effect is not degraded. For example, when carrying out fractionation, it is sufficient that a fraction with which the growth-promoting effect can be attained is used as the active ingredient. Examples of fractionation include removal of cells and isolation of an objective substance. That is, for example, when using the Bacillus bacterium for fermentative production of an objective substance such as an amino acid or nucleic acid, the objective substance may be appropriately collected from the culture broth and separately used, and the remaining part, such as the fermentation by-product may be used as described herein. Examples of sterilization include heat sterilization and filter sterilization. These treatments can be independently used, or can be used in an appropriate combination. That is, examples of the culture broth used as the active ingredient include the actual culture broth of the bacterium, a culture supernatant separated from the culture broth, and processed products thereof. Examples of the processed products include products subjected to such a treatment as mentioned above, e.g. condensation, dilution, fractionation, sterilization, or a combination thereof. Incidentally, although the term "culture broth" is used for convenience of explanation, the active ingredient also includes products that take a form other than a liquid form as a result of such a treatment as mentioned above, such as a condensed dried product. The culture broths of such embodiments can be independently used as the active ingredient, or can be used as the active ingredient in an appropriate combination.

<3>Composition

The composition as described herein is an agricultural or horticultural composition containing the active ingredient (i.e. containing the culture broth as described herein).

The term "agricultural or horticultural composition" refers to a composition used for cultivation of a plant, such as agriculture or horticulture. The term "agricultural or horticultural composition" also includes a fertilizer and an agrichemical. That is, the composition may be configured as a fertilizer or an agrichemical.

The composition can be used by application of the same to a plant. The method using of the composition as described herein is described in detail in section entitled "Method". By using the composition as described herein, specifically, by applying the composition to a plant, growth of the plant can be promoted, that is, the growth-promoting effect can be obtained. That is, the composition may be a composition for promoting growth of a plant. A composition for promoting growth of a plant is also referred to as "growth-promoting agent for a plant".

The composition may consist of only the active ingredient, or may contain an ingredient other than the active ingredient. That is, the active ingredient may be used as the composition as it is, or may be used as the composition in combination with another ingredient.

The ingredient(s) other than the active ingredient is not particularly limited, so long as the growth-promoting effect is not degraded. As the ingredient other than the active ingredient, ingredients acceptable depending on the purpose of use of the composition can be used. Examples of the ingredient other than the active ingredient include, for example, ingredients generally used for a use of agrochemical, fertilizer, medicament, etc. Specific examples of such ingredients include additives such as excipients, binders, disintegrants, lubricants, stabilizers, diluents, surfactants, spreaders, pH adjusters, water, alcohols, vitamins, and minerals. As the ingredient other than the active ingredient, one kind of ingredient may be used, or two or more kinds of ingredients may be used.

The form of the composition is not particularly limited. The composition may take any form such as a form of powder, granule, liquid, paste, or cube. The composition may be formulated to a desired form. The composition may be provided as a form applicable to a plant as it is, or may be prepared in a form applicable to a plant before use.

The amounts and the ratio of the ingredients, such as the active ingredient and, as desired, other ingredient(s), in the composition are not particularly limited, so long as the growth-promoting effect can be obtained. The amounts and the ratio of ingredients in the composition can be appropriately set according to various conditions such as the embodiment of the active ingredient, the type(s) of the other ingredient(s), the type of the target plant, and the type of use of the composition.

The amount of the active ingredient in the composition, for example, may be 0.01% (w/w) or higher, 0.1% (w/w) or higher, 1% (w/w) or higher, 5% (w/w) or higher, or 10% (w/w) or higher, may be 100% (w/w) or lower, 99.9% (w/w) or lower, 70% (w/w) or lower, 50% (w/w) or lower, 30% (w/w) or lower, 10% (w/w) or lower, 5% (w/w) or lower, or 1% (w/w) or lower, or may be within a range defined as a non-contradictory combination thereof.

Furthermore, the amount of the active ingredient in the composition, for example, in terms of the amount of the original culture broth, may be 0.01% (w/w) or higher, 0.1% (w/w) or higher, 1% (w/w) or higher, 5% (w/w) or higher, or 10% (w/w) or higher, may be 10000% (w/w) or lower, 5000% (w/w) or lower, 1000% (w/w) or lower, 500% (w/w) or lower, 300% (w/w) or lower, 200% (w/w) or lower, 150% (w/w) or lower, 100% (w/w) or lower, 70% (w/w) or lower, 50% (w/w) or lower, 30% (w/w) or lower, 10% (w/w) or lower, 5% (w/w) or lower, or 1% (w/w) or lower, or may be within a range defined as a non-contradictory combination thereof. The term "original culture broth" refers to a culture broth in which a change in the concentration, such as condensation or dilution, has not occurred during the culture, and may specifically refer to a culture broth as it exists immediately after the culture, that is, the actual culture broth of the bacterium. Incidentally, an amount over 100% (w/w) means that the culture broth is present in the composition in a condensed form. That is, for example, an amount of 200% (w/w) means that the culture broth is present in the composition in a 2-fold condensed form.

Furthermore, the amount of the active ingredient in the composition may be, for example, an amount that results in an application amount of the active ingredient within a desired range. Specifically, the amount of the active ingredient in the composition may be, for example, an amount that results in an application amount of the active ingredient within a desired range when applying the active ingredient to a plant by using the composition. The application amount of the active ingredient may be within such a range as described herein.

When the composition contains two or more kinds of ingredients, the ingredients may be present as a mixture in the composition, or each of the ingredients or any combination of the ingredients may be separately present in the composition.

<4>Method

The method as described herein is a method including a step of applying the active ingredient (i.e. containing the culture broth as described herein) to a plant.

By the method, specifically, by applying the active ingredient to a plant, growth of the plant can be promoted, that is, the growth-promoting effect can be obtained. That is, the method as described herein may be a method for promoting growth of a plant.

The active ingredient can be applied to a plant by, for example, using the composition, for example, by applying the composition. That is, an embodiment of the method may be, for example, a method including a step of applying the composition to a plant. The phrase "applying the active ingredient to a plant" also includes applying the composition to a plant. That is, for example, when the active ingredient is the actual culture broth of the bacterium, a culture supernatant separated from the culture broth, or a processed product thereof, such as a condensed product, diluted product, or fractionated product, the phrase "applying the active ingredient to a plant" also includes applying the composition containing the active ingredient in such a form to a plant. The composition may be applied to a plant, for example, as it is, or after being appropriately diluted, dispersed, or dissolved with a liquid such as water, physiological saline, buffers, and alcohols. That is, the composition may be applied to a plant, for example, after appropriately adjusting the concentration of the composition so that the concentration of the active ingredient is within a certain range. The composition may be applied to a plant, particularly, in a form of liquid. The concentration of the active ingredient upon application of the composition is also referred to as "application concentration of the active ingredient". For the application concentration of the active ingredient, for example, the descriptions concerning the amount of the active ingredient in the composition can be similarly applied. The application concentration of the active ingredient, for example, particularly, in terms of the concentration of the original culture broth, may be 0.01% (w/w) or higher, 0.1% (w/w) or higher, 1% (w/w) or higher, 5% (w/w) or higher, or 10% (w/w) or higher, may be 150% (w/w) or lower, 100% (w/w) or lower, 70% (w/w) or lower, 50% (w/w) or lower, 30% (w/w) or lower, 10% (w/w) or lower, 5% (w/w) or lower, or 1% (w/w) or lower, or may be within a range defined as a non-contradictory combination thereof. The application concentration of the active ingredient may be, for example, particularly, in terms of the concentration of the original culture broth, 0.01% (w/w) to 150% (w/w), 0.1% (w/w) to 150% (w/w), 1% (w/w) to 150% (w/w), 5% (w/w) to 150% (w/w), 0.01% (w/w) to 100% (w/w), 0.01% (w/w) to 70% (w/w), 0.01% (w/w) to 50% (w/w), 0.1% (w/w) to 70% (w/w), or 1% (w/w) to 50% (w/w). In addition, the composition may be used in combination with another ingredient. For the other ingredient, the descriptions concerning the ingredient other than the active ingredient in the composition can be similarly applied. That is, the composition may be used in combination with, for example, an additive such as a spreader.

The application method of the composition is not particularly limited, so long as the growth-promoting effect can be obtained. The application method of the composition can be appropriately set according to various conditions such as the type of the target plant, the cultivation method of the target plant, and the growth stage of the target plant. The composition can be applied to a plant by, for example, a usual method for applying an agrochemical or fertilizer to a plant. The composition, for example, may be applied to a plant body, may be applied to soil or a medium to be used for cultivation of the plant, or may be applied to a combination thereof. Examples of application to the plant body include spraying or spreading to the plant body, and immersion of the plant body. The composition may be applied to the entire or a part of the plant body. The composition may be applied to, for example, all of the above-ground part of the plant body. Examples of a part of the plant body include leaf, stalk, stems, root, and fruit. When applying the composition to a leaf, the composition may be applied to either the front or the back surface of the leaf, or may be applied to both surfaces. Specific examples of application to the plant body include leaf spraying and root immersion. Examples of application to the soil or medium include spraying, irrigation, or mixing to the soil or medium. It is sufficient that application to the soil or medium is carried out so that the active ingredient reaches the rhizosphere of the plant.

The application timing of the composition is not particularly limited, so long as the growth-promoting effect can be obtained. The application timing of the composition can be appropriately set according to various conditions such as the type of the target plant and the cultivation method of the target plant. The composition may be applied during a period from germination of the plant to completion of growth of the plant. Examples of the period from germination to completion of growth include a period when root formation is proceeding. The composition may specifically be applied to, for example, a sprout of the plant. The composition may be applied only once, or may be applied twice or more. The composition may be applied intermittently, or may be applied continuously.

The application amount of the composition is not particularly limited, so long as the growth-promoting effect can be obtained. The application amount of the composition can be appropriately set according to various conditions such as the type of the target plant, the cultivation method of the target plant, the growth stage of the target plant, and the application method and application timing of the composition.

The application amount of the composition, for example, in terms of the application amount of the original culture broth, may be 1 L/ha or more, 1.5 L/ha or more, 3 L/ha or more, 5 L/ha or more, 10 L/ha or more, 100 L/ha or more, 200 L/ha or more, 500 L/ha or more, 1000 L/ha or more, 1500 L/ha or more, 3000 L/ha or more, or 5000 L/ha or more, may be 10000 L/ha or less, 8000 L/ha or less, 7000 L/ha or less, 5000 L/ha or less, 3000 L/ha or less, 1500 L/ha or less, 1000 L/ha or less, 700 L/ha or less, 500 L/ha or less, 300 L/ha or less, 200 L/ha or less, 150 L/ha or less, or 100 L/ha or less, or may be within a range defined as a non-contradictory combination thereof. The application amount of the composition may specifically be, for example, in terms of the application amount of the original culture broth, 1 L/ha to 10000 L/ha, 1 L/ha to 1000 L/ha, 1 L/ha to 500 L/ha, 10 L/ha to 10000 L/ha, 100 L/ha to 10000 L/ha, 200 L/ha to 8000 L/ha, 500 L/ha to 5000 L/ha, or 1000 L/ha to 3000 L/ha. In addition, the application amount of the composition may be set in consideration of not only the application area (two-dimensional element) but also the three-dimensional element. The application amount of the composition may specifically be, for example, in terms of the application amount of the original culture broth, 1 L/ha to 1500 L/ha or 1 L/ha to 150 L/ha for a plant of ground to knee-high, 1 L/ha to 3000 L/ha or 1.5 L/ha to 300 L/ha for a plant of knee-high to human height, 1 L/ha to 5000 L/ha or 3 L/ha to 500 L/ha for a plant of human height to 2 meters, or 1 L/ha to 7000 L/ha or 5 L/ha to 700 L/ha for a plant of over 2 meters. Such an application amount of the composition as exemplified above may be an application amount upon applying the composition to a plant by spraying to the plant body, such as leaf spraying, or by spraying to the soil or medium.

Furthermore, the application amount of the composition may be, for example, in terms of the application amount of the original culture broth, an amount resulting in a concentration of the active ingredient in the rhizosphere of the plant to be within such a use concentration of the active ingredient as exemplified above. Examples of the concentration of the active ingredient in the rhizosphere of the plant include the concentration in the soil and the concentration in the medium.

The descriptions concerning such an application embodiment of the composition as described above can be similarly applied to any other cases of applying the active ingredient to a plant. That is, for example, the active ingredient may be applied to a plant at such a application concentration as exemplified above. Furthermore, for example, the active ingredient may be applied to a plant in such an application amount of the active ingredient as exemplified above. The active ingredient may be applied to a plant, for example, as it is, or after being appropriately prepared as a composition containing the active ingredient. For the composition containing the active ingredient, the descriptions concerning the composition can be similarly applied. The active ingredient may be applied to a plant, particularly, in a form of liquid. That is, the active ingredient may be applied to a plant, specifically, for example, after being appropriately prepared as a liquid composition containing the active ingredient. The active ingredient may be applied to a plant, more specifically, for example, after being appropriately prepared as a liquid composition containing the active ingredient at such a use concentration as exemplified above. In addition, the active ingredient may be used in combination with another ingredient.

Incidentally, by cultivating a plant by using the method as described herein, a plant body can be obtained. Hence, an embodiment of the method may also be a method for producing a plant body. More specifically, an embodiment of the method may also be a method for producing a plant body, the method including the steps of applying the active ingredient (i.e. containing the culture broth as described herein) to a plant to cultivate the plant. Cultivation of the plant can be carried out by, for example, the same method as a usual method used for cultivation of plants, except that the active ingredient is applied. The plant body can be appropriately collected. That is, the method may further include collecting the plant body. The plant body to be collected may be the entire or a part of the plant body. Examples of a part of the plant body include leaf, stalk, stems, root, and fruit.

<5>Use of the Active Ingredient

Furthermore, use of the active ingredient is provided for such a purpose as described above. That is, for example, use of the active ingredient for promotion of growth of a plant, or use of the active ingredient for production of a composition for promoting growth of a plant. Furthermore, the active ingredient is provided for use in such a purpose as described above. That is, for example, the active ingredient is provided for use in promotion of growth of a plant, or the active ingredient is provided for use in production of a composition for promoting growth of a plant.

EXAMPLES

Hereinafter, the present invention will be more specifically explained with reference to non-limiting examples.

<1>Acquisition of p-Fluoro-Phenylalanine Resistant Strains of *Bacillus amyloliquefaciens*

The *Bacillus amyloliquefaciens* strains AJ11708 (NITE BP-02609) and FZB42 (DSM 23117) as parent strains were each cultured on an agar-medium containing 0.4 g/L f-Phe (p-fluoro-phenylalanine), and the grown f-Phe strains were isolated. As a result of determining mutation sites of these f-Phe resistant strains, it was found that they have the following mutations in PheA (prephenate dehydratase): one AJ11708-derived f-Phe resistant strain (AG14924=VKPM B12841=AJ111345 strain (NITE BP-02610), PheA (F247Y)), and four FZB42-derived f-Phe resistant strains (AG15091=VKPM B12834-2 strain, PheA(S213L); AG15092=VKPM B12834-3 strain, PheA(N229Y); AG15093=VKPM B12834-4 strain, PheA(S213L); AG15094=VKPM B12834-5 strain, PheA(S213L)). Culture broths of these f-Phe resistant strains were subjected to TLC analysis or amino acid analysis, and as a result, it was revealed that the accumulation amount of Phe in the culture broths was increased as compared with that in culture broths of the respective parent strains. Hence, these f-Phe resistant strains were considered as strains in which feedback inhibition of PheA by phenylalanine has been reduced or eliminated, i.e. strains having inhibition-resistant PD. Incidentally, these f-Phe resistant strains can also be obtained reproducibly by, for example, introducing the aforementioned mutations into PDs of the aforementioned parent strains by genetic engineering techniques.

The *Bacillus amyloliquefaciens* AJ11708 strain (NITE BP-02609) was deposited at the independent administrative agency, National Institute of Technology and Evaluation, Patent Microorganisms Depositary (NPMD) (#122, 2-5-8 Kazusakamatari, Kisarazu-shi, Chiba-ken, 292-0818, Japan) as an international deposit under the provisions of the Budapest Treaty on Jan. 11, 2018, and assigned an accession number of NITE BP-02609.

The *Bacillus amyloliquefaciens* AJ111345 strain (NITE BP-02610) was deposited at the independent administrative agency, National Institute of Technology and Evaluation, Patent Microorganisms Depositary (NPMD) (#122, 2-5-8 Kazusakamatari, Kisarazu-shi, Chiba-ken, 292-0818, Japan) as an international deposit under the provisions of the Budapest Treaty on Jan. 11, 2018, and assigned an accession number of NITE BP-02610.

<2>Preparation and Application of Culture Broth Samples

The parent strains and f-Phe resistant strains of *Bacillus amyloliquefaciens* were each inoculated into 20 mL of a medium (Table 1) contained in a 300-mL flask, and culture was carried out for 2 days at 34° C. with rotation at 150 rpm. The culture broth was centrifuged to collect a culture supernatant. The culture supernatant was subjected to filter sterilization with a 0.22-μm filter to obtain a culture broth sample.

TABLE 1

| | |
|---|---|
| $NH_4Cl$ | 20 g/L |
| Yeast Extract (Bio Springer) | 1 g/L |
| $KH_2PO_4$ | 1 g/L |
| $MgSO_4 \cdot 7H_2O$ | 0.4 g/L |
| $MnSO_4 \cdot 5H_2O$ 1.0 w/v % solution | 1.53 mL/L |
| $FeSO_4 \cdot 7H_2O$ | 0.01 g/L |
| Thiamin-HCl | 0.01 g/L |
| Glucose | 60 g/L |
| adjusted to pH7.0 (1N KOH) | |
| $CaCO_3$ (separately sterilized*) | 30 g/L |

*$CaCO_3$ was preliminarily put in a culture vessel and sterilized, and a required amount of the liquid medium adjusted to pH7.0 with 1N KOH and then subjected to filter sterilization with a 0.22-μm filter was added thereto.

*Arabidopsis thaliana* sprouts grown for 4 days in a sterile gellan gum medium (0.5% gellan gum) containing 1% sucrose and MS inorganic salts was inoculated to a sterile gellan gum medium (0.5% gellan gum) containing 1% sucrose and MS inorganic salts and added with the culture broth sample of each strain at a final concentration of 1%. The sprouts grown for 7 days after the inoculation were tested for the number of lateral roots (n=6). In addition, an increase in the fresh weight of a plant can be measured by, for example, carrying out cultivation in the same manner on the same medium added with the culture broth sample of each strain at a final concentration of 0.01 to 1%.

<3>Results

Results (average±SD) are shown in FIG. 1. An increase in the number of lateral roots of *Arabidopsis thaliana* sprouts was observed when applying the culture broth samples of the f-Phe resistant strains, i.e. strains having inhibition-resistant PD, as compared with when applying the culture broth samples of the wild-type strains. That is, it was revealed that application of a culture broth of a *Bacillus* bacterium having inhibition-resistant PD can improve growth of a plant.

INDUSTRIAL APPLICABILITY

According to the present invention, an agricultural or horticultural composition can be provided.

<Explanation of Sequence Listing>

SEQ ID NOS:

1: Nucleotide sequence of wild-type PD gene of *Bacillus amyloliquefaciens* AJ11708

2: Amino acid sequence of wild-type PD of *Bacillus amyloliquefaciens* AJ11708

3: Nucleotide sequence of wild-type PD gene of *Bacillus amyloliquefaciens* FZB42

4: Amino acid sequence of wild-type PD of *Bacillus amyloliquefaciens* FZB42

5: Nucleotide sequence of wild-type PD gene of *Escherichia coli* K-12 MG1655

6: Amino acid sequence of wild-type PD of *Escherichia coli* K-12 MG1655

7: Nucleotide sequence of wild-type PD gene of *Brevibacterium lactofermentum* AJ12125

8: Amino acid sequence of wild-type PD of *Brevibacterium lactofermentum* AJ12125

The invention claimed is:

1. A method for promoting growth of a plant, the method comprising: applying a composition comprising: a culture broth of a *Bacillus* bacterium, a culture supernatant separated from the culture broth, or a processed product of the culture broth or the culture supernatant, wherein said composition has prephenate dehydratase that is resistant to feedback inhibition by phenylalanine to the plant; wherein the prephenate dehydratase has a mutation at a position relative to the wild-type prephenate dehydratase.

2. The method according to claim 1, wherein the *Bacillus* bacterium is *Bacillus amyloliquefaciens* or *Bacillus velezensis*.

3. The method according to claim 1, wherein the composition is the culture broth of the *Bacillus* bacterium.

4. The method according to claim 3, wherein the processed product is a product subjected to condensation, dilution, fractionation, sterilization, or a combination thereof.

5. The method according to claim 1, wherein the culture broth is applied to soil or a medium.

6. The method according to claim 1, wherein the culture broth is applied in an amount of 1 L/ha to 10000 L/ha immediately after completion of the culture.

7. The method according to claim 1, wherein the culture broth is applied so that the concentration of the culture broth in the rhizosphere of the plant is 0.01% (w/w) to 150% (w/w) immediately after completion of the culture.

8. The method according to claim 1, wherein the mutation is at a position, relative to the wild-type prephenate dehydratase, selected from the group consisting of:
   A) S213,
   B) N229,
   C) F247, and
   D) combinations thereof.

9. The method according to claim 8, wherein the mutation is selected from the group consisting of:
   A) S213L,
   B) N229Y,
   C) F247Y, and
   D) combinations thereof.

10. The method according to claim 8, wherein the wild-type prephenate dehydratase is selected from the group consisting of:
   (a) a protein comprising the amino acid sequence of SEQ ID NO: 2 or 4;
   (b) a protein comprising the amino acid sequence of SEQ ID NO: 2 or 4, but which includes substitution, deletion, insertion, and/or addition of 1 to 10 amino acid residues; and
   (c) a protein comprising an amino acid sequence having an identity of 90% or higher to the amino acid sequence of SEQ ID NO: 2 or 4.

11. A method for producing a plant body, the method comprising:

applying a culture broth of a *Bacillus* bacterium having prephenate dehydratase that is resistant to feedback inhibition by phenylalanine to a plant to cultivate the plant; and collecting the plant body;

wherein the prephenate dehydratase has a mutation at a position relative to the wild-type prephenate dehydratase.

* * * * *

SEQUENCE LISTING

<160> NUMBER OF SEQ ID NOS: 8

<210> SEQ ID NO 1
<211> LENGTH: 858
<212> TYPE: DNA
<213> ORGANISM: Bacillus amyloliquefaciens

<400> SEQUENCE: 1

| | |
|---|---:|
| atgaaagtcg gttatttagg gccagaagcc acatttacac atctagcagt cagttcctgc | 60 |
| tttcaaaaca gcgtgacaca agcacccttat catacaatac cggcatgcat ggatgcggcg | 120 |
| gtcgcgggag aagttgatct tgcgtttgtt cccttggaaa acgcgctgga gggctctgtt | 180 |
| aacttaacga ttgactactt aattcatgag cagcccccttg cgatcgtggg ggaaatgacg | 240 |
| ctgccgatcc accagcacct gctcgttcac ccttcgaaaa aaaatgagtg gaaacagctt | 300 |
| gagaaaattt attctcattc acatgcgatt gcgcaatgcc acaaatttct tcaccggcat | 360 |
| ttttcggccg ttccttatga gtatgcgaag tcaaccggtg cggctgctaa gtatgtgagt | 420 |
| gagcacccgg aacttccgat cggcgtgatt gcaaatgaaa tggcggccgc tacatacgga | 480 |
| ttgagcatcg tgaggcggga cattcaggat tatcaggata accacacgag atttgtcatt | 540 |
| ctttcacctg aaaaagacgt atcatttgaa gtgagtgcga aactgtcttc acggccgaaa | 600 |
| acgacgatga tggtgacgct tccccaagat gaccaatcag gcgcgctgca cagggtgctg | 660 |
| tccgcttttt catggagaaa ccttaattta tcaagatcg aatcgcgccc gacaaaaacg | 720 |
| ggtctcggca actatttctt tattattgat attgaacagg cgatggatca ggtgctgatt | 780 |
| cccggtgccg ttcaagagat ggaagccctc ggctgccggg tcaagcttct gggaacatat | 840 |
| caatcctatt ccatataa | 858 |

<210> SEQ ID NO 2
<211> LENGTH: 285
<212> TYPE: PRT
<213> ORGANISM: Bacillus amyloliquefaciens

<400> SEQUENCE: 2

Met Lys Val Gly Tyr Leu Gly Pro Glu Ala Thr Phe Thr His Leu Ala
1               5                   10                  15

Val Ser Ser Cys Phe Gln Asn Ser Val Thr Gln Ala Pro Tyr His Thr
            20                  25                  30

Ile Pro Ala Cys Met Asp Ala Ala Val Ala Gly Glu Val Asp Leu Ala
        35                  40                  45

Phe Val Pro Leu Glu Asn Ala Leu Glu Gly Ser Val Asn Leu Thr Ile
    50                  55                  60

Asp Tyr Leu Ile His Glu Gln Pro Leu Ala Ile Val Gly Glu Met Thr
65                  70                  75                  80

Leu Pro Ile His Gln His Leu Leu Val His Pro Ser Lys Glu Asn Glu
                85                  90                  95

Trp Lys Gln Leu Glu Lys Ile Tyr Ser His Ser His Ala Ile Ala Gln
            100                 105                 110

Cys His Lys Phe Leu His Arg His Phe Ser Ala Val Pro Tyr Glu Tyr
        115                 120                 125

Ala Lys Ser Thr Gly Ala Ala Ala Lys Tyr Val Ser Glu His Pro Glu
    130                 135                 140

Leu Pro Ile Gly Val Ile Ala Asn Glu Met Ala Ala Ala Thr Tyr Gly
145                 150                 155                 160

Leu Ser Ile Val Arg Arg Asp Ile Gln Asp Tyr Gln Asp Asn His Thr

```
            165                 170                 175
Arg Phe Val Ile Leu Ser Pro Glu Lys Asp Val Ser Phe Glu Val Ser
            180                 185                 190

Ala Lys Leu Ser Ser Arg Pro Lys Thr Thr Met Met Val Thr Leu Pro
            195                 200                 205

Gln Asp Gln Ser Gly Ala Leu His Arg Val Leu Ser Ala Phe Ser
    210                 215                 220

Trp Arg Asn Leu Asn Leu Ser Lys Ile Glu Ser Arg Pro Thr Lys Thr
225                 230                 235                 240

Gly Leu Gly Asn Tyr Phe Phe Ile Ile Asp Ile Glu Gln Ala Met Asp
                245                 250                 255

Gln Val Leu Ile Pro Gly Ala Val Gln Glu Met Glu Ala Leu Gly Cys
            260                 265                 270

Arg Val Lys Leu Leu Gly Thr Tyr Gln Ser Tyr Ser Ile
            275                 280                 285

<210> SEQ ID NO 3
<211> LENGTH: 858
<212> TYPE: DNA
<213> ORGANISM: Bacillus amyloliquefaciens

<400> SEQUENCE: 3
atgaaagtcg gttatttagg gccagaagcc acatttacac atctagcagt cagttcctgc     60
tttcaaaaca gcgtgacaca agcaccttat caaacaatac cggcatgcat ggatgcggcg    120
gttgcgggag aagttgatct tgcatttgtt cctttggaaa acgcgctgga aggctcggtt    180
aacttaacga ttgactattt gattcatgag cagcctcttg cgatcgtggg ggaaatgacg    240
ctgccgattc accagcatct gctcgttcac ccttcgagag aaaatgagtg gaaaagctt    300 gagaaaattt attctcattc ccatgcgatt gcgcaatgcc acaaatttct tcaccggcat    360
ttttcgtccg ttccttatga gtatgcgaag tcaacaggtg cggctgccaa gtatgtcagt    420
gagcattcgg accttccgat cggcgtgatt gcaaatgaaa tggccgccgc tacatacgga    480
ttgagcatcg tgaagcggga tattcaggat tatcaggaca accacacgag atttgtcatt    540
ctttcgcctg aaaaagacgt ctcattcgaa gtgaatgcga aactgtcttc acggccgaaa    600
acgacgatga tggtaacgct tccccaagat gaccaatcag gtgcgctgca cagggtgctg    660
tccgcttttt catggagaaa cctgaattta tcaaagatcg aatcgcgccc gacaaaaacg    720
ggtctcggca actatttctt tattattgat attgaacagg cgatggatca ggttctcatt    780
cccggtgccg ttcaagagat ggaagccctc ggctgccggg tcaagcttct gggaacatat    840
caatcctatt cgatataa                                                   858

<210> SEQ ID NO 4
<211> LENGTH: 285
<212> TYPE: PRT
<213> ORGANISM: Bacillus amyloliquefaciens

<400> SEQUENCE: 4

Met Lys Val Gly Tyr Leu Gly Pro Glu Ala Thr Phe Thr His Leu Ala
1               5                   10                  15

Val Ser Ser Cys Phe Gln Asn Ser Val Thr Gln Ala Pro Tyr Gln Thr
            20                  25                  30

Ile Pro Ala Cys Met Asp Ala Ala Val Ala Gly Glu Val Asp Leu Ala
        35                  40                  45

Phe Val Pro Leu Glu Asn Ala Leu Glu Gly Ser Val Asn Leu Thr Ile
```

```
                    50                  55                  60
Asp Tyr Leu Ile His Glu Gln Pro Leu Ala Ile Val Gly Glu Met Thr
 65                  70                  75                  80

Leu Pro Ile His Gln His Leu Leu Val His Pro Ser Arg Glu Asn Glu
                     85                  90                  95

Trp Lys Lys Leu Glu Lys Ile Tyr Ser His Ser His Ala Ile Ala Gln
                100                 105                 110

Cys His Lys Phe Leu His Arg His Phe Ser Ser Val Pro Tyr Glu Tyr
            115                 120                 125

Ala Lys Ser Thr Gly Ala Ala Ala Lys Tyr Val Ser Glu His Ser Asp
        130                 135                 140

Leu Pro Ile Gly Val Ile Ala Asn Glu Met Ala Ala Thr Tyr Gly
145                 150                 155                 160

Leu Ser Ile Val Lys Arg Asp Ile Gln Asp Tyr Gln Asp Asn His Thr
                165                 170                 175

Arg Phe Val Ile Leu Ser Pro Glu Lys Asp Val Ser Phe Glu Val Asn
            180                 185                 190

Ala Lys Leu Ser Ser Arg Pro Lys Thr Thr Met Met Val Thr Leu Pro
        195                 200                 205

Gln Asp Asp Gln Ser Gly Ala Leu His Arg Val Leu Ser Ala Phe Ser
210                 215                 220

Trp Arg Asn Leu Asn Leu Ser Lys Ile Glu Ser Arg Pro Thr Lys Thr
225                 230                 235                 240

Gly Leu Gly Asn Tyr Phe Phe Ile Ile Asp Ile Glu Gln Ala Met Asp
                245                 250                 255

Gln Val Leu Ile Pro Gly Ala Val Gln Glu Met Glu Ala Leu Gly Cys
            260                 265                 270

Arg Val Lys Leu Leu Gly Thr Tyr Gln Ser Tyr Ser Ile
        275                 280                 285

<210> SEQ ID NO 5
<211> LENGTH: 1161
<212> TYPE: DNA
<213> ORGANISM: Escheichia coli

<400> SEQUENCE: 5
atgacatcgg aaaacccgtt actggcgctg cgagagaaaa tcagcgcgct ggatgaaaaa     60
ttattagcgt tactggcaga acggcgcgaa ctggccgtcg aggtgggaaa agccaaactg    120
ctctcgcatc gcccggtacg tgatattgat cgtgaacgcg atttgctgga agattaatt    180 acgctcggta aagcgcacca tctggacgcc cattacatta ctcgcctgtt ccagctcatc    240
attgaagatt ccgtattaac tcagcaggct ttgctccaac aacatctcaa taaaattaat    300
ccgcactcag cacgcatcgc ttttctcggc cccaaaggtt cttattccca tcttgcggcg    360
cgccagtatg ctgcccgtca ctttgagcaa ttcattgaaa gtggctgcgc caaatttgcc    420
gatattttta atcaggtgga aaccggccag gccgactatg ccgtcgtacc gattgaaaat    480
accagctccg gtgccataaa cgacgtttac gatctgctgc aacataccag cttgtcgatt    540
gttggcgaga tgacgttaac tatcgaccat tgtttgttgg tctccggcac tactgattta    600
tccaccatca atacggtcta cagccatccg cagccattcc agcaatgcag caaattcctt    660
aatcgttatc cgcactggaa gattgaatat accgaaagta cgtctgcggc aatggaaaag    720
gttgcacagg caaaatcacc gcatgttgct gcgttgggaa cgaagctgg cggcactttg    780 tacggtttgc aggtactgga gcgtattgaa gcaaatcagc gacaaaactt cacccgattt    840
```

-continued

```
gtggtgttgg cgcgtaaagc cattaacgtg tctgatcagg ttccggcgaa aaccacgttg    900
ttaatggcga ccgggcaaca agccggtgcg ctggttgaag cgttgctggt actgcgcaac    960
cacaatctga ttatgacccg tctggaatca cgcccgattc acggtaatcc atgggaagag   1020
atgttctatc tggatattca ggccaatctt gaatcagcgg aaatgcaaaa agcattgaaa   1080
gagttagggg aaatcacccg ttcaatgaag gtattgggct gttacccaag tgagaacgta   1140
gtgcctgttg atccaacctg a                                              1161
```

<210> SEQ ID NO 6
<211> LENGTH: 386
<212> TYPE: PRT
<213> ORGANISM: Escheichia coli

<400> SEQUENCE: 6

```
Met Thr Ser Glu Asn Pro Leu Leu Ala Leu Arg Glu Lys Ile Ser Ala
1               5                   10                  15

Leu Asp Glu Lys Leu Leu Ala Leu Leu Ala Glu Arg Arg Glu Leu Ala
            20                  25                  30

Val Glu Val Gly Lys Ala Lys Leu Leu Ser His Arg Pro Val Arg Asp
        35                  40                  45

Ile Asp Arg Glu Arg Asp Leu Leu Glu Arg Leu Ile Thr Leu Gly Lys
    50                  55                  60

Ala His His Leu Asp Ala His Tyr Ile Thr Arg Leu Phe Gln Leu Ile
65                  70                  75                  80

Ile Glu Asp Ser Val Leu Thr Gln Gln Ala Leu Leu Gln Gln His Leu
                85                  90                  95

Asn Lys Ile Asn Pro His Ser Ala Arg Ile Ala Phe Leu Gly Pro Lys
            100                 105                 110

Gly Ser Tyr Ser His Leu Ala Ala Arg Gln Tyr Ala Ala Arg His Phe
        115                 120                 125

Glu Gln Phe Ile Glu Ser Gly Cys Ala Lys Phe Ala Asp Ile Phe Asn
    130                 135                 140

Gln Val Glu Thr Gly Gln Ala Asp Tyr Ala Val Val Pro Ile Glu Asn
145                 150                 155                 160

Thr Ser Ser Gly Ala Ile Asn Asp Val Tyr Asp Leu Leu Gln His Thr
                165                 170                 175

Ser Leu Ser Ile Val Gly Glu Met Thr Leu Thr Ile Asp His Cys Leu
            180                 185                 190

Leu Val Ser Gly Thr Thr Asp Leu Ser Thr Ile Asn Thr Val Tyr Ser
        195                 200                 205

His Pro Gln Pro Phe Gln Gln Cys Ser Lys Phe Leu Asn Arg Tyr Pro
    210                 215                 220

His Trp Lys Ile Glu Tyr Thr Glu Ser Thr Ser Ala Ala Met Glu Lys
225                 230                 235                 240

Val Ala Gln Ala Lys Ser Pro His Val Ala Ala Leu Gly Ser Glu Ala
                245                 250                 255

Gly Gly Thr Leu Tyr Gly Leu Gln Val Leu Glu Arg Ile Glu Ala Asn
            260                 265                 270

Gln Arg Gln Asn Phe Thr Arg Phe Val Val Leu Ala Arg Lys Ala Ile
        275                 280                 285

Asn Val Ser Asp Gln Val Pro Ala Lys Thr Thr Leu Leu Met Ala Thr
    290                 295                 300

Gly Gln Gln Ala Gly Ala Leu Val Glu Ala Leu Leu Val Leu Arg Asn
```

```
                305                 310                 315                 320
His Asn Leu Ile Met Thr Arg Leu Glu Ser Arg Pro Ile His Gly Asn
                    325                 330                 335

Pro Trp Glu Glu Met Phe Tyr Leu Asp Ile Gln Ala Asn Leu Glu Ser
                340                 345                 350

Ala Glu Met Gln Lys Ala Leu Lys Glu Leu Gly Glu Ile Thr Arg Ser
            355                 360                 365

Met Lys Val Leu Gly Cys Tyr Pro Ser Glu Asn Val Val Pro Val Asp
        370                 375                 380

Pro Thr
385

<210> SEQ ID NO 7
<211> LENGTH: 948
<212> TYPE: DNA
<213> ORGANISM: Brevibacterium lactofermentum

<400> SEQUENCE: 7
atgagcgacg caccaattgt tgtggcctat ttggggcctg ccggaacctt caccgaagaa      60
gccctctaca aatttgccga cgccggcgta ttcggcgacg gtgagatcga gcagctacca     120
gccaaatcgc cacaagaagc tgtcgacgcg gtccgccacg gcaccgccca gttcgcggtg     180
gtcgccatcg aaaacttcgt cgacggcccc gtcaccccca ccttcgacgc ccttgaccag     240
ggctccaacg tgcaaatcat cgccgaagaa gaactcgata ttgccttttc catcatggtc     300
cggccaggga cttcgcttgc cgacgtcaaa accctcgcca cccacccggt tgggtaccaa     360
caagtgaaaa actggatggc aaccaccatt ccggacgcca tgtatctttc agcaagctcc     420
aacggcgccg cgcacaaaat ggttgccgaa ggaaccgccg acgcagccgc agcgccctcc     480
cgcgcagccg aactcttcgg actggaacgc cttgttgatg atgtcgccga cgtccgcggc     540
gcccgcaccc gcttcgttgc agtccaagcc caagcagccg tttccgaacc gaccggccac     600
gaccgcacct ccgtcatttt ctccctaccg aatgtgccag gcagcctcgt gcgcgccctc     660
aacgaattcg ccatccgtgg cgtcgacctc acccgcatcg aatcccgccc cacccgcaaa     720
gtcttcggaa cctaccgctt ccacctggac atatccggac atatccgcga catccccgtc     780
gccgaagccc tccgcgcact ccacctccaa gccgaagaac tcgtattcgt cggttcctgg     840
cccctccaacc gtgcagaaga cagcacgccc caaaccgacc aactagctaa cgtacacaag     900
gcggacgaat gggttcgcgc agcaagcgaa ggaaggaaac ttaactag                  948

<210> SEQ ID NO 8
<211> LENGTH: 315
<212> TYPE: PRT
<213> ORGANISM: Brevibacterium lactofermentum

<400> SEQUENCE: 8

Met Ser Asp Ala Pro Ile Val Val Ala Tyr Leu Gly Pro Ala Gly Thr
1               5                  10                  15

Phe Thr Glu Glu Ala Leu Tyr Lys Phe Ala Asp Ala Gly Val Phe Gly
            20                  25                  30

Asp Gly Glu Ile Glu Gln Leu Pro Ala Lys Ser Pro Gln Glu Ala Val
        35                  40                  45

Asp Ala Val Arg His Gly Thr Ala Gln Phe Ala Val Val Ala Ile Glu
    50                  55                  60

Asn Phe Val Asp Gly Pro Val Thr Pro Thr Phe Asp Ala Leu Asp Gln
65                  70                  75                  80
```

```
-continued

Gly Ser Asn Val Gln Ile Ile Ala Glu Glu Glu Leu Asp Ile Ala Phe
            85              90                  95

Ser Ile Met Val Arg Pro Gly Thr Ser Leu Ala Asp Val Lys Thr Leu
            100             105             110

Ala Thr His Pro Val Gly Tyr Gln Gln Val Lys Asn Trp Met Ala Thr
        115             120             125

Thr Ile Pro Asp Ala Met Tyr Leu Ser Ala Ser Ser Asn Gly Ala Gly
    130             135             140

Ala Gln Met Val Ala Glu Gly Thr Ala Asp Ala Ala Ala Pro Ser
145             150             155             160

Arg Ala Ala Glu Leu Phe Gly Leu Glu Arg Leu Val Asp Val Ala
            165             170             175

Asp Val Arg Gly Ala Arg Thr Arg Phe Val Ala Val Gln Ala Gln Ala
            180             185             190

Ala Val Ser Glu Pro Thr Gly His Asp Arg Thr Ser Val Ile Phe Ser
        195             200             205

Leu Pro Asn Val Pro Gly Ser Leu Val Arg Ala Leu Asn Glu Phe Ala
    210             215             220

Ile Arg Gly Val Asp Leu Thr Arg Ile Glu Ser Arg Pro Thr Arg Lys
225             230             235             240

Val Phe Gly Thr Tyr Arg Phe His Leu Asp Ile Ser Gly His Ile Arg
            245             250             255

Asp Ile Pro Val Ala Glu Ala Leu Arg Ala Leu His Leu Gln Ala Glu
            260             265             270

Glu Leu Val Phe Val Gly Ser Trp Pro Ser Asn Arg Ala Glu Asp Ser
        275             280             285

Thr Pro Gln Thr Asp Gln Leu Ala Asn Val His Lys Ala Asp Glu Trp
    290             295             300

Val Arg Ala Ala Ser Glu Gly Arg Lys Leu Asn
305             310             315
```